US012778358B2

(12) United States Patent
Huang

(10) Patent No.: US 12,778,358 B2
(45) Date of Patent: Nov. 3, 2026

(54) FABRIC TOWEL DISPENSER

(71) Applicant: Wei Huang, Irvine, CA (US)

(72) Inventor: Wei Huang, Irvine, CA (US)

( * ) Notice: Subject to any disclaimer, the term of this patent is extended or adjusted under 35 U.S.C. 154(b) by 101 days.

(21) Appl. No.: 18/982,972

(22) Filed: Dec. 16, 2024

(65) Prior Publication Data

US 2026/0165540 A1 Jun. 18, 2026

(51) Int. Cl.

*A61L 2/10* (2026.01)
*A47K 10/28* (2006.01)
*A61L 103/50* (2026.01)

(52) U.S. Cl.

CPC ................ *A47K 10/28* (2013.01); *A61L 2/10* (2013.01); *A61L 2103/50* (2026.01)

(58) Field of Classification Search

CPC ...................................................... A47K 10/28
See application file for complete search history.

(56) References Cited

U.S. PATENT DOCUMENTS

| | | | | |
|---|---|---|---|---|
| 8,607,472 B2 * | 12/2013 | Ishii | A47K 10/48 | 34/526 |
| 2008/0093497 A1 * | 4/2008 | Helland | A47K 10/46 | 312/34.11 |
| 2014/0263394 A1 * | 9/2014 | Horian | A47G 21/12 | 221/192 |
| 2016/0353947 A1 * | 12/2016 | Osborne, Jr. | B65H 20/02 | |

* cited by examiner

*Primary Examiner* — Gene O Crawford
*Assistant Examiner* — Ayodeji H Ojofeitimi
(74) *Attorney, Agent, or Firm* — Hemisphere Law, PLLC

(57) ABSTRACT

The present disclosure relates to a fabric towel dispenser, including a housing and a support shaft. The housing includes a shell, a backplate, and a middle plate. The backplate and the middle plate are fixedly positioned relative to the shell. The middle plate and the shell enclose a cavity configured to accommodate a fabric towel. The support shaft passes through the middle plate, with one end connected to the backplate. This configuration allows the support shaft to be jointly supported by the middle plate and the backplate. Additionally, at least part of the support shaft is suspended on a side of the middle plate facing away from the backplate, so as to support the fabric towel.

13 Claims, 8 Drawing Sheets

FABRIC TOWEL DISPENSER

FIELD OF INVENTION

The present disclosure relates to the technical field of hand-drying devices, specifically to a fabric towel dispenser.

BACKGROUND

Fabric towel dispensers are typically installed in restrooms to provide clean fabric towels for users to dry their hands after washing. Traditional towel dispensers generally include a housing, one or more support shafts mounted within the housing, drive rollers, and several guide rods. When the drive roller rotates, it pulls the towel strip out through the dispensing outlet of the housing. The users can dry their hands with the exposed towel. Once the user finishes using the towel, the corresponding support shaft rotates to retract the used towel strip back into the housing.

In conventional fabric towel dispensers, towel rolls often have considerable weight. To ensure the stability of the towel roll inside the housing, both ends of the support shaft are supported by internal structures of the housing. One end of the shaft is connected to the housing, and a robust support structure is typically required at the opposite end of the shaft to provide stable support for the fabric. This design results in a relatively complex and bulky dispenser structure, requiring significant installation space.

SUMMARY

The embodiments of the present disclosure provide a fabric towel dispenser that ensures the stability and convenience of fabric roll installation while simplifying the device structure and enhancing compactness.

A fabric towel dispenser includes:

- a housing, which includes a shell, a back plate, and a middle plate, where the back plate and the middle plate are fixed relative to the shell, and the middle plate and the shell form a cavity to accommodate a fabric towel; and
- a support shaft, which passes through the middle plate, with one end connected to the back plate, where the back plate and the middle plate jointly support the support shaft, and at least part of the support shaft is suspended on a side of the middle plate away from the back plate to support the fabric towel.

This design minimizes the need for additional internal structures, improving compactness while maintaining installation stability.

BRIEF DESCRIPTION OF THE DRAWINGS

To better illustrate the technical solutions of the present disclosure or the prior art, a brief introduction to the drawings used in the descriptions of the embodiments or prior art is provided below. It is apparent that the drawings mentioned below are merely examples of some embodiments of the present disclosure. Those skilled in the art could derive additional drawings without creative effort based on these examples.

These illustrations provide clear guidance on the structure and functionality of the fabric towel dispenser in various states.

DETAILED DESCRIPTION OF THE EMBODIMENTS

The following detailed description of the preferred embodiment is the preferred mode of carrying out the present disclosure. The description is not to be taken in any limiting sense. It is presented for the purpose of illustrating the general principles of the present disclosure.

It should be appreciated that the terms "install", "connect", "couple", and "mount" in the following description refer to the connecting relationship in the accompanying drawings for easy understanding of the present disclosure. For example, the connection can refer to permanent connection or detachable connection. Furthermore, "connected" may also mean direct connection or indirect connection, or connection through other auxiliary components. Therefore, the above terms should not be an actual connection limitation of the elements of the present disclosure.

It should be appreciated that the terms "length", "width", "top", "bottom", "front", "rear", "left", "right", vertical", "horizontal", "upper", "lower", "exterior", and "interior" in the following description refer to the orientation or positioning relationship in the accompanying drawings for easy understanding of the present disclosure without limiting the actual location or orientation of the present disclosure. Therefore, the above terms should not be an actual location limitation of the elements of the present disclosure.

It should be appreciated that the terms "first", "second", "one", "a", and "an" in the following description refer to "at least one" or "one or more" in the embodiment. In particular, the term "a" in one embodiment may refer to "one" while in another embodiment may refer to "more than one". Therefore, the above terms should not be an actual numerical limitation of the elements of the present disclosure.

To facilitate understanding of the present disclosure, a more comprehensive description of the present disclosure will be provided below with reference to the relevant drawings. The drawings present preferred embodiments of the present disclosure. However, the present disclosure may be implemented in many different forms and is not limited to the embodiments described herein. Instead, these embodiments are provided to make the disclosure of the present disclosure more thorough and comprehensive.

Figure 1:
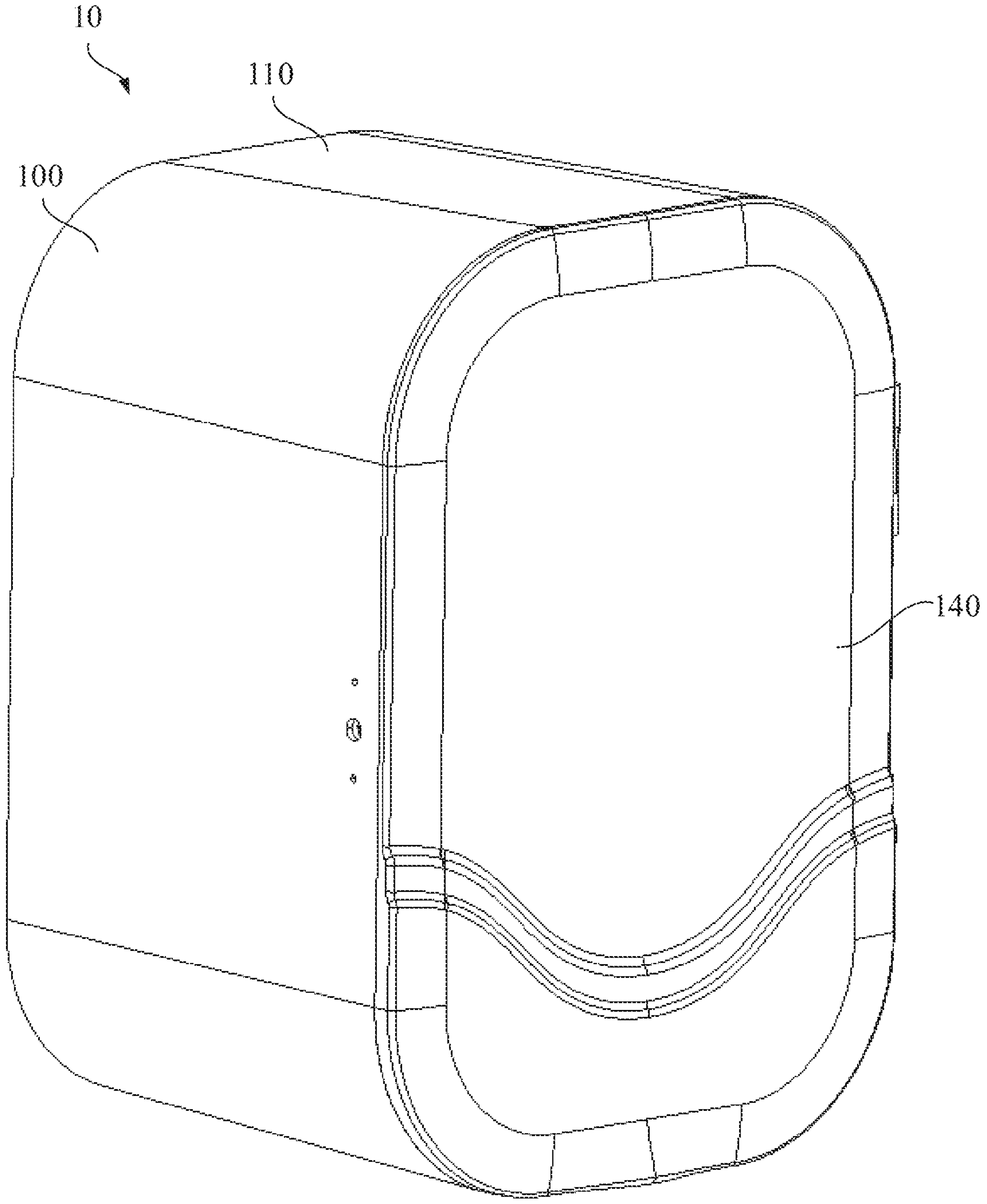
FIG. 1 is a schematic diagram of a fabric towel dispenser with a panel in a closed state according to an embodiment of the present disclosure.
Figure 2:
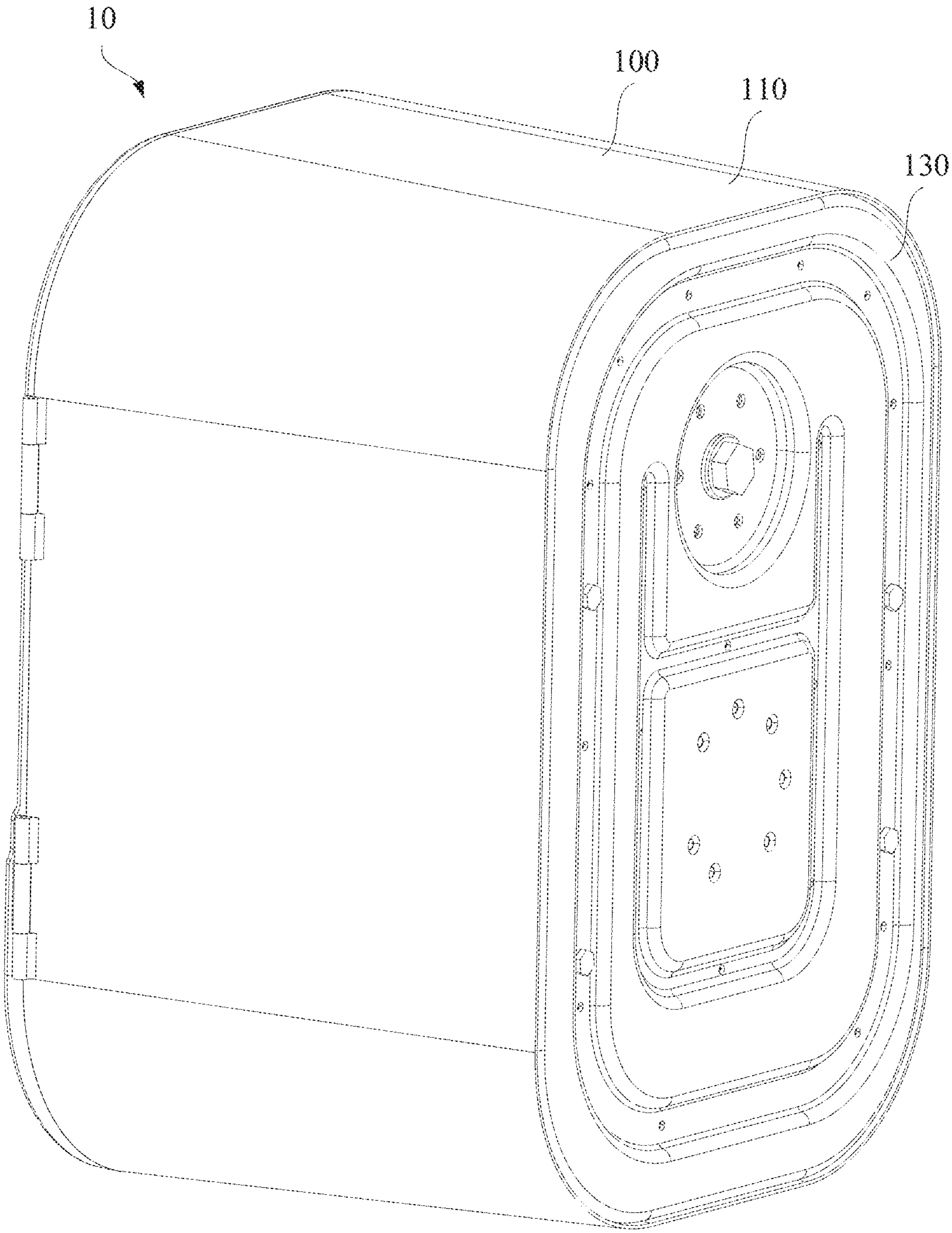
FIG. 2 is a schematic diagram of the fabric towel dispenser with the panel in a closed state shown in FIG. 1 from another perspective.

Referring to FIGS. 1 and 2, this application discloses a fabric towel dispenser 10, which can be installed in environments like restrooms to provide wiping fabric towels for users. The fabric towel used in the fabric towel dispenser 10 of this application is not limited to cloth towels, but may also be relatively thick or highly absorbent tissues or other materials.

Figure 3:
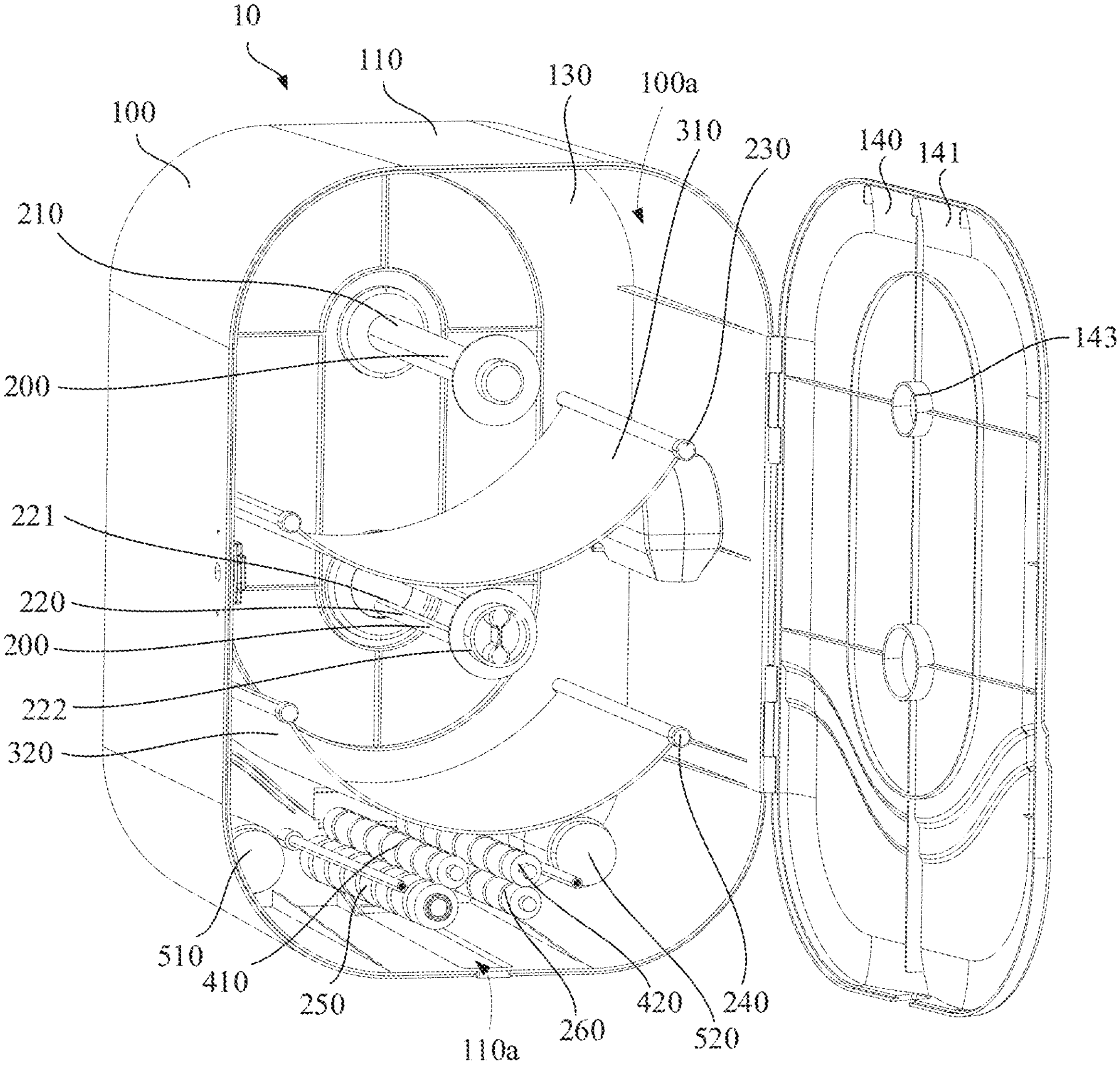
FIG. 3 is a schematic diagram of a fabric towel dispenser with a panel in an open state, after removing part of its structure according to an embodiment of the present disclosure.
Figure 4:
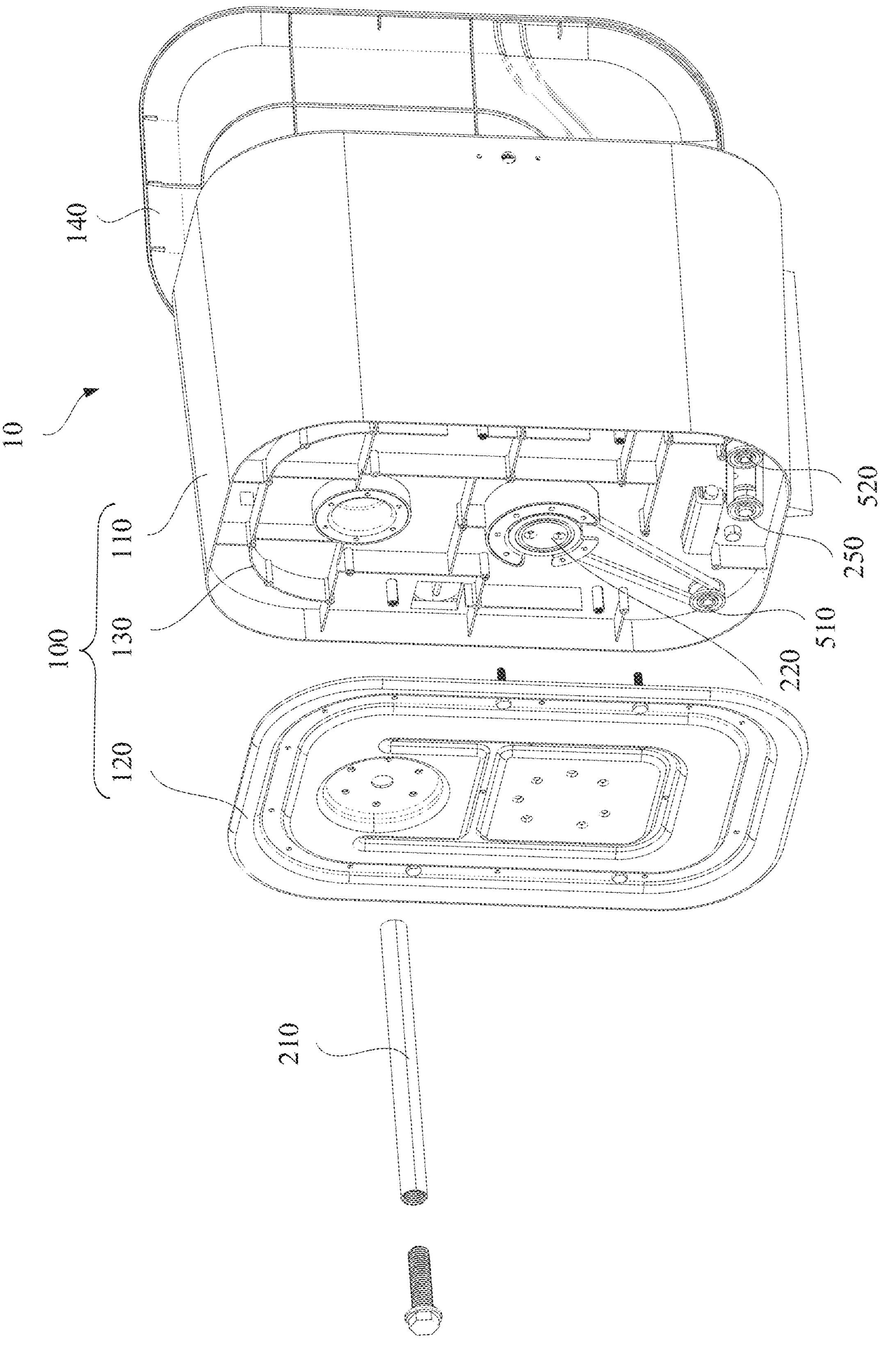
FIG. 4 is an exploded view of a fabric towel dispenser with a panel in an open state according to an embodiment of the present disclosure.
Figure 5:
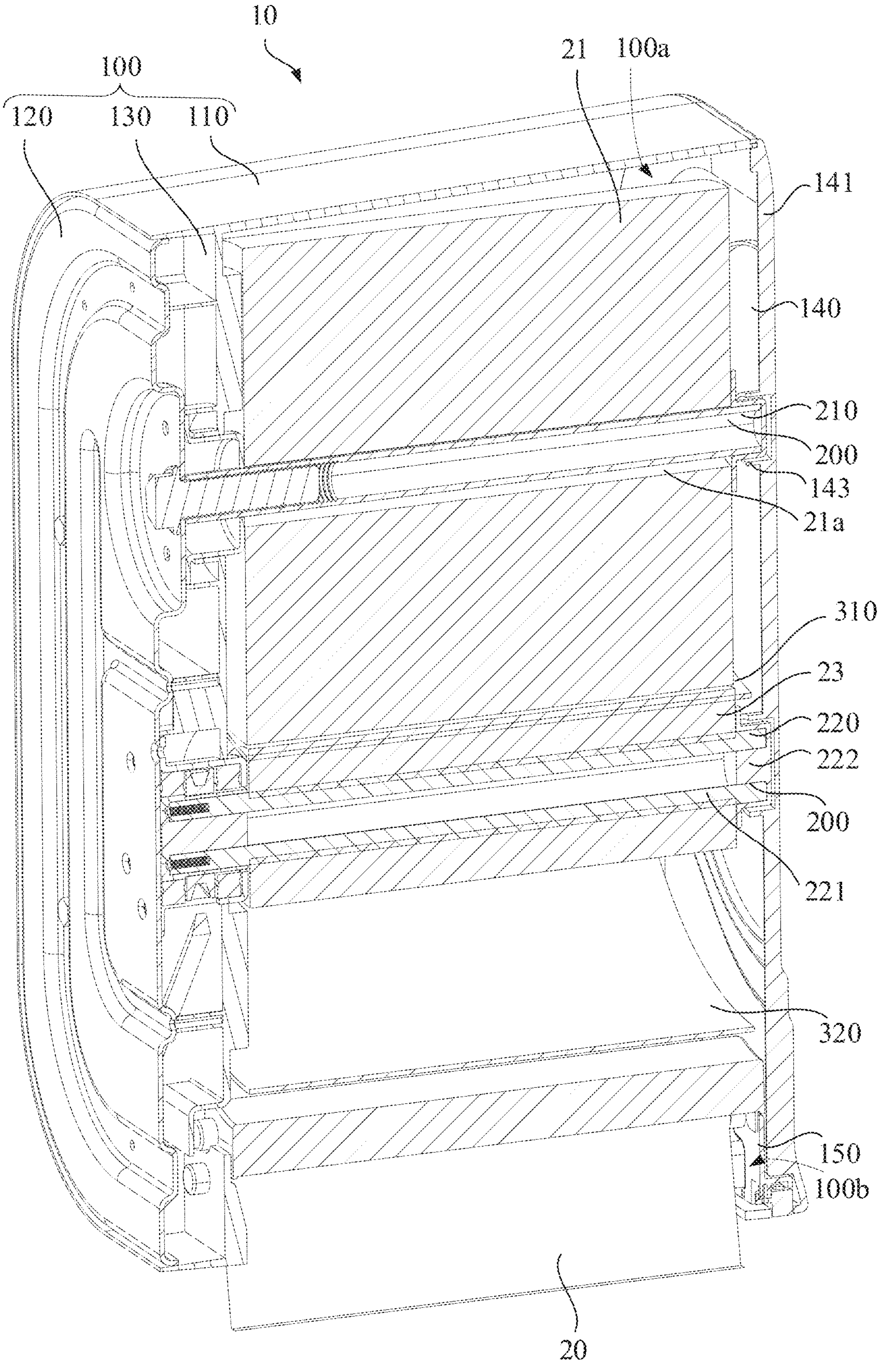
FIG. 5 is a cross-sectional view of a fabric towel dispenser with a panel in a closed state according to an embodiment of the present disclosure.

In conjunction with FIGS. 3, 4, and 5, the fabric towel dispenser 10 may include a housing 100 and a support shaft 200. The housing 100 includes a shell 110, a backplate 120, and a middle plate 130. The shell 110 can be in a rounded rectangular frame shape, or a rectangular frame shape, or an ellipse frame shape, etc. The backplate 120 and the middle plate 130 are fixed relative to the shell 110, and the middle plate 130 and the shell 110 enclose a cavity 100*a* for holding a fabric towel 20. The backplate 120 and the shell 110 can be welded together, or can use snap fasteners or threaded fasteners to achieve a detachable connection. The middle plate 130 and the shell 110 can be integrally molded, or they can use snap fasteners or threaded fasteners to achieve a detachable connection. For example, the middle plate 130 and the shell 110 are injection molded, and the backplate 120 is detachably connected to the middle plate 130 or the shell 110 through threaded fasteners, thereby ensuring that the backplate 120 and the middle plate 130 are fixed relative to the shell 110. In some embodiments, the support shaft 200 is perpendicular to at least one of the backplate 120 and the middle plate 130 and perpendicular to a mounting wall, and there may be one or more support shafts 200. The support shaft 200 can also be further subdivided into a releasing shaft 210 and a collecting shaft 220, as detailed later.

In some embodiments, a depth of the cavity 100*a*, which is a distance between an end of the shell 110 facing away from the backplate 120 and the middle plate 130, is greater than a distance between the middle plate 130 and the backplate 120. That is, a side of the middle plate 130 facing away from the backplate 120 has a relatively larger accommodation space. The larger accommodation space can be used to install a fabric roll 21 to be used, and provide space for collect a used fabric roll 23.

Continuing to refer to FIG. 5, the support shaft 200 is installed through the middle plate 130, with one end connected to the backplate 120, such that the support shaft 200 is supported by both the middle plate 130 and the backplate 120, with at least part of the support shaft 200 suspended on the side of the middle plate 130 facing away from the backplate 120 to support the fabric towel 20.

In some embodiments, a side of the backplate 120 facing away from the middle plate 130 can form a recessed or protruding mounting structure for installing the end of the support shaft 200. The support shaft 200 can be rotatably connected to the backplate 120, so as through rolling bearings or sliding bearings, to reduce the resistance during the movement of the fabric towel 20. Of course, this type of support shaft 200 can also be fixedly connected to the backplate 120 to simplify the connection structure.

Referring to FIG. 4, various reinforcement ribs and shaft sleeves can be set on the side of the middle plate 130 facing the backplate 120, which enhances the structural strength of the middle plate 130 while saving material costs, reducing weight, and increasing internal space. At the same time, large flanges and many screws are used at the connection points between the support shaft 200, the middle plate 130, and the backplate 120 to help share the torque borne by the middle plate 130 and backplate 120, ensuring that the support shaft 200 is firmly and stably fixed on the middle plate 130 and the backplate 120. The space between the backplate 120 and the middle plate 130 can be used for configuring transmission structures such as belts or chains, utilizing a motor and a transmission belt to drive one or more support shafts 200 to rotate, either to move the unused new fabric towel 20 out of the housing 100, or to collect the used fabric towel 20 back into the housing 100. This arrangement simplifies the structure inside the cavity 100*a* and provides convenience for users to install a fabric roll 21 to be used and collect a used fabric roll 23.

The middle plate 130 and the backplate 120 can provide leverage support for the support shaft 200. For the support shaft 200 that rotates relative to the backplate 120, rolling bearings or sliding bearings can be used to connect the support shaft 200 to the middle plate 130, ensuring smooth rotation of the support shaft 200. For those support shafts 200 that provide auxiliary support, when they are rotatably connected to the backplate 120, bearings can be used to connect them to the backplate 120 and the middle plate 130. When they are fixed to the backplate 120, they can be directly inserted into the backplate 120 and the middle plate 130 to provide support.

Furthermore, in some embodiments, the structural strength of the backplate 120 may be greater than that of the middle plate 130. For example, the backplate 120 may be made of stainless steel, while the middle plate 130 may be made of plastic. The backplate 120, with its higher strength, forms a stronger structural support for the support shaft 200, while the middle plate 130, with relatively lower strength, serves as an auxiliary support point. Together, the two provide stable support for the support shaft 200. At the same time, the support shaft 200 can be made of a larger diameter and high-strength metal material, providing sufficient rigidity and strength to prevent excessive deformation of the support shaft 200 during use, which may otherwise cause operational issues.

In some embodiments, the support shaft 200 includes a collecting shaft 220, which may include at least two rods 221 that can open and close relative to each other, and a collecting shaft sleeve 222 that fits onto free ends of the rods 221. During the initial setup of the fabric towel 20's path, the user can manually pull one end of the fabric roll 21 to guide it along the set path through the various guide rods (first guide rod 230, second guide rod 240) and drive rollers (FIG. 3, first roller 250) in the fabric towel dispenser 10. The initial section of the fabric towel 20 is passed through the rods 221, and the drive motor (collecting motor 510 in FIG. 3) is activated to rotate the rods 221, causing part of the fabric towel 20 to be wound onto the rods 221, forming a fabric roll. Afterward, during the operational phase, as new fabric towel 20 is continuously released and used, the used fabric towel 20 will be collected and wound onto the collecting shaft 220, causing the diameter of the used fabric towel roll 23 to increase. Eventually, when all the fabric towel 20 has been used and is entirely wound onto the used fabric towel roll 23, a panel 140 of the fabric towel dispenser 10 can be opened, the collecting shaft sleeve 222 is removed, and the entire used fabric roll 23 is pulled off the rods 221. Then, the collecting shaft sleeve 222 is reinstalled on the rods 221. The collecting shaft sleeve 222 serves to assist in fixing the position of the rods 221 and enhances the rigidity of the entire collecting shaft 220, while also acting as a stopper and limit for the used fabric towel 20 and used fabric roll 23. In other embodiments, the collecting shaft 220 may use other structures to clamp the fabric towel 20, such as openable clips or locking mechanisms. During the fabric guiding phase, the initial section of the fabric towel 20 can be clamped, and when the used fabric towel roll 23 needs to be removed, the lock or elastic ring can be opened to extract the entire used fabric roll 23.

Continuing with reference to FIGS. 3 and 5, in some embodiments, the support shaft 200 may include a releasing shaft 210, which is parallel to and spaced apart from the collecting shaft 220. The fabric roll 21 to be used is mounted on the releasing shaft 210, allowing the fabric roll 21 to rotate more easily on the releasing shaft 210, reducing the resistance of the new fabric towel 20 as it moves and lowering the energy consumption of a releasing motor 520. For example, the fabric roll 21 includes a shaft core 21*a* and the new fabric towel 20 wound onto the shaft core 21*a*. The releasing shaft 210 is inserted into the shaft core 21*a*, with the shaft core 21*a* and the releasing shaft 210 being in a clearance fit.

Of course, the shaft core 21*a* of the fabric roll 21 to be used is not mandatory. For example, the fabric roll 21 to be used can form a hollow cavity in its core area, which can be directly fitted onto the releasing shaft 210 via the hollow cavity, with a clearance fit between the two. In some embodiments, the releasing shaft 210 may be fixed to the middle plate 130 and the backplate 120, and the fabric roll 21 to be used can be driven to rotate by the releasing motor 520. In other embodiments, the releasing shaft 210 may be rotatably connected to the middle plate 130 and the back plate 120 via bearings, allowing the fabric roll 21 to be used and the releasing shaft 210 to rotate together when driven by the releasing motor 520. This configuration reduces the resistance when the fabric roll 21 to be used releases fabric 20, thereby lowering the energy consumption of the fabric towel dispenser 10.

Figure 6:
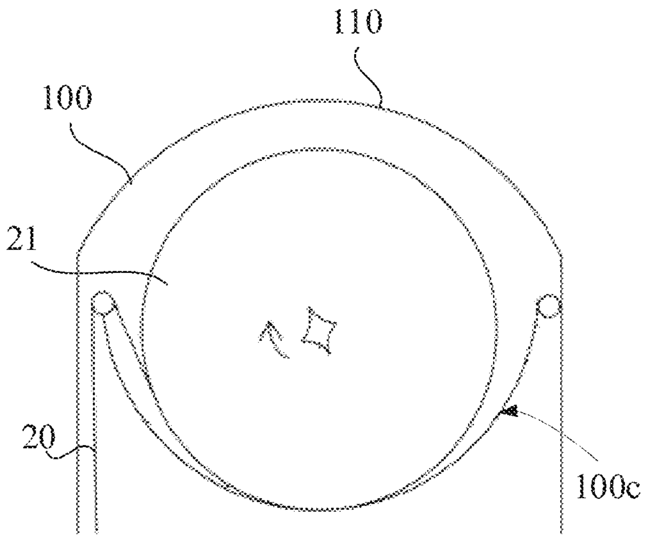
FIG. 6 is a schematic diagram of the relative position of the fabric roll to be used and the support slot in the fabric towel dispenser according to an embodiment of the present disclosure.

With reference to FIG. 6, it can be understood that in other embodiments, the releasing shaft 210 may not be included, and the fabric roll 21 to be used can simply be placed in a support slot 100*c*. In this case, the releasing motor 520 will pull the fabric towel 20 for dispensing, and the fabric roll 21 to be used will rotate in the support slot 100*c*. The support slot 100*c* can also serve to separate the fabric roll 21 to be used from the used fabric roll 23. In this embodiment, the fabric towel dispenser 10 does not require the releasing shaft 210, simplifying the structure of the fabric towel dispenser 10. However, the rotation of the fabric roll 21 to be used may experience greater frictional resistance from the support slot 100*c*, which could increase the energy consumption of the releasing motor 520 and impose higher rigidity requirements on the corresponding support structure.

Figure 7:
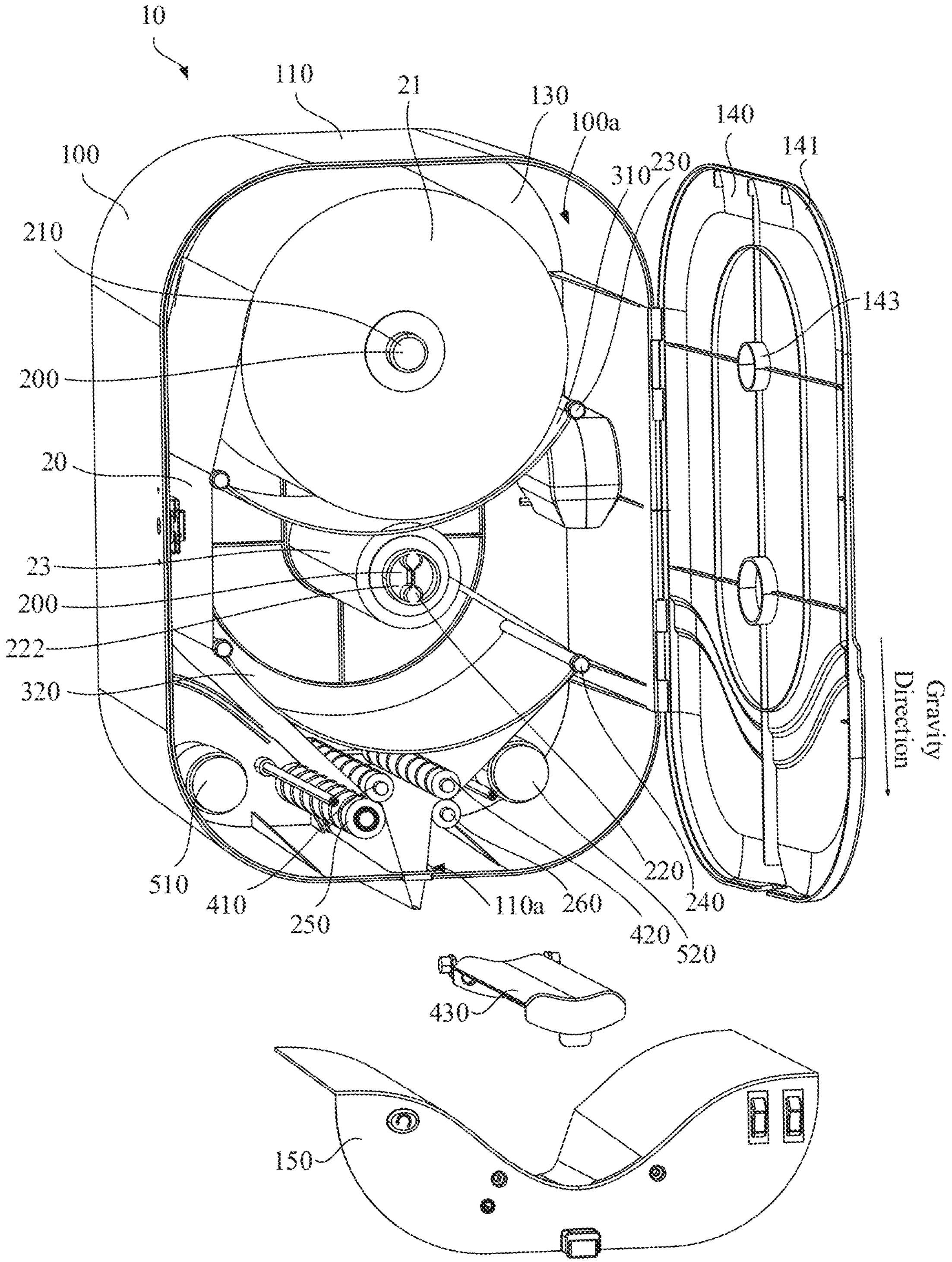
FIG. 7 is an exploded view of a fabric towel dispenser with a panel in an open state according to an embodiment of the present disclosure.

With reference to FIGS. 3 and 7, in some embodiments, the fabric towel dispenser 10 includes a panel 140 rotatably connected to the shell 110, which switches between open and closed states relative to the shell 110. In the open state, the releasing shaft 210 and the collecting shaft 220 are exposed. As shown in FIG. 1, in the closed state, the panel 140 covers the cavity 100*a*. The panel 140 may include a plate body 141 and a limit member 143 protruding from an inner side of the plate body 141. In the closed state, the limit member 143 restricts a swing range of free ends of both the releasing shaft 210 and collecting shaft 220.

Specifically, the plate body 141 is plate-shaped, and its inner side may have two limit members 143 spaced apart and protruding from the plate body 141. One limit member 143 has a slot that matches the shape of the free end of the collecting shaft 220, and the size of the slot is slightly larger than the size of the collecting shaft sleeve 222. The other limit member 143 has a slot that matches the shape of the free end of the releasing shaft 210, and the size of the slot is slightly larger than the size of the free end of the releasing shaft 210. After the panel 140 covers the cavity 100*a*, the two limit members 143 correspondingly accommodate the free ends of the collecting shaft sleeve 222 and the releasing shaft 210, ensuring a gap between the collecting shaft sleeve 222 and the sidewall of the slot, and a gap between the free end of the releasing shaft 210 and the sidewall of the slot, thereby restricting the swing range of the free ends of both the releasing shaft 210 and the collecting shaft 220.

The limit members 143 restrict the swing range of the free end of the collecting shaft 220, preventing it from swinging at large angles that could affect the normal operation of the fabric towel dispenser 10. This ensures the long-term stable operation of the fabric towel dispenser 10 and enhances its service life. In the embodiment where the releasing shaft 210 can rotate relative to the housing 100, this structure prevents interference with the rotation of the releasing shaft 210 or the formation of excessive resistance. In the embodiment where the releasing shaft 210 is fixed relative to the housing 100, this structure also limits the swing range of the releasing shaft 210 caused by the new fabric towel 20 to be used, preventing large-angle swings that may affect the fabric towel dispenser's normal operation. Thus, it ensures the long-term stable operation of the fabric towel dispenser 10 and improves its lifespan.

It is understood that the limit members 143 on the panel 140 limit the swing range of the free ends of both the releasing shaft 210 and the collecting shaft 220. In the absence of limit members 143, the releasing shaft 210 and the collecting shaft 220 can still meet rigidity requirements, meaning that the limit members 143 on the panel 140 can be optional.

With reference to FIGS. 3 and 5, in the embodiment of the present application, the bottom of the shell 110 may have a fabric towel outlet 110*a* for dispensing the fabric towel 20. When the fabric towel dispenser 10 is installed on a wall or similar support, the releasing shaft 210, collecting shaft 220, and fabric towel outlet 110*a* are arranged roughly along the direction of gravity, with the collecting shaft 220 being closer to the fabric towel outlet 110*a* than the releasing shaft 210 in the gravity direction. This arrangement prevents drops of liquid from the used fabric towel roll 23 from falling onto the new fabric roll 21 under gravity, thereby preventing contamination or wetting of the new fabric roll 21, and ensuring that the new fabric roll 21 remains clean and hygienic. It is understood that in other embodiments, the releasing shaft 210 or new fabric roll 21 may also be positioned closer to the fabric towel outlet 110*a*.

Furthermore, the fabric towel dispenser 10 may include a first flexible partition 310 located within the cavity 100*a*. The fabric towel dispenser 10 includes two parallel and spaced first guide rods 230, and two ends of the first flexible partition 310 are respectively sleeved or fixed onto the two first guide rods 230. The first flexible partition 310 is positioned between the releasing shaft 210 and the collecting shaft 220. The first flexible partition 310 can be made from materials such as plastic, rubber, silicone, or metal, and it has certain flexibility or elasticity. It can be in an arc shape and protrude outward toward the fabric towel outlet 110*a*, thus providing a space for the unused fabric roll 21. Additionally, the structure of the first flexible partition 310 may be designed such that the user can easily remove it from the cavity 100*a* to install the unused fabric roll 21 or collect the used fabric towel roll 23, thereby enhancing the convenience of use, which will not be elaborated here. The first flexible partition 310 can also prevent the used fabric towel roll 23 from contaminating the unused fabric roll 21. In other implementations, the two ends of the first flexible partition 310 may adopt other fixing and assembly methods, such as being fixed to a separately provided rod or support.

Specifically, in some embodiments, the first flexible partition 310 has better elastic deformation or bending deformation properties, for example, it may have a corrugated shape or other bendable and stretchable forms. The first flexible partition 310 can press against the unused fabric roll 21 and change its bending curvature in response to changes in the radial size of the unused fabric roll 21. For instance, in its natural state, the arc length and bending degree of the first flexible partition 310 may be small. When a new unused fabric roll 21 is installed on the releasing shaft 210, the unused fabric roll 21 can drive the first flexible partition 310 to undergo a larger or different bending deformation to press against the unused fabric roll 21. As the new fabric towel 20 is gradually released, the radial size of the unused fabric roll 21 decreases, and the deformation of the first flexible partition 310 is gradually restored. On the one hand, this structure of the first flexible partition 310 can ensure the stable release of the new fabric towel 20, preventing excessive fabric towel 20 from being pulled away from the unused fabric roll 21 due to inertia and accumulating in the cavity 100*a*, interfering with the movement of other moving parts. On the other hand, the structure of the first flexible partition 310 can deform adaptively according to the changes in the radial size of the unused fabric roll 21, thus reducing the gap between the releasing shaft 210 and the collecting shaft 220, fully utilizing the installation space within the shell 110, enhancing the compactness of the fabric towel dispenser 10, and reducing the overall size of the fabric towel dispenser 10.

Of course, the first flexible partition 310 can also be used to press against the used fabric towel roll 23 and change its bending curvature as the radial size of the used fabric towel roll 23 changes, ensuring the stability of the winding of the used fabric towel 20 and reducing the gap between the releasing shaft 210 and the collecting shaft 220, fully utilizing the installation space within the shell 110, enhancing the compactness of the fabric towel dispenser 10, and reducing the overall size of the fabric towel dispenser 10.

It can be understood that in other embodiments, the first flexible partition 310 may simply have better bending deformation properties, and the first flexible partition 310 may not be used to continuously press against the unused fabric roll 21. Instead, it will change its bending direction and curvature in response to the radial size changes of the used fabric towel roll 23.

It can be understood that in other embodiments, the first flexible partition 310 may also be rigid, or take other shell forms, but its function remains to separate the unused fabric roll 21 and the used fabric towel roll 23.

The fabric towel dispenser 10 may also include a second flexible partition 320 located within the cavity 100*a*. For example, the fabric towel dispenser 10 includes two parallel and spaced second guide rods 240. Two ends of the second flexible partition 320 are respectively sleeved onto the two second guide rods 240, and the second flexible partition 320 is positioned between the collecting shaft 220 and the fabric towel outlet 110*a*. The second flexible partition 320 can be made from materials such as plastic, rubber, silicone, or metal, and it has certain flexibility and elasticity. It can be in an arc shape and protrude outward toward the fabric towel outlet 110*a*, thus providing a space for the used fabric towel roll 23. The two ends of the second flexible partition 320 may be provided with shaft sleeve structures to be sleeved onto the second guide rods 240, thereby reliably positioning the second flexible partition 320 within the cavity 100*a*. When pulling a towel from the unused fabric roll 21 for the initial fabric towel path setup, the second flexible partition 320 can be manually lifted to provide more space for easier fabric towel path operation.

In other embodiments, the second flexible partition 320 may also have better elastic deformation or bending deformation properties, such as having a corrugated shape or other bendable and stretchable forms, and it can press against the unused fabric roll 21 and change its bending curvature according to the changes in the radial size of the used fabric towel roll 23.

In some embodiments, the user can also remove the second flexible partition 320 from the cavity 100*a* to provide more space for easier fabric towel path operation. In other embodiments, the two ends of the second flexible partition 320 may adopt other fixing and assembly methods, such as being fixed to a separately provided rod or support.

It can be understood that in other embodiments, the second flexible partition 320 may also be rigid or take other shell forms, but its function remains to separate the used fabric towel roll 23 and lower components and structures of the fabric towel dispenser 10.

Figure 8:
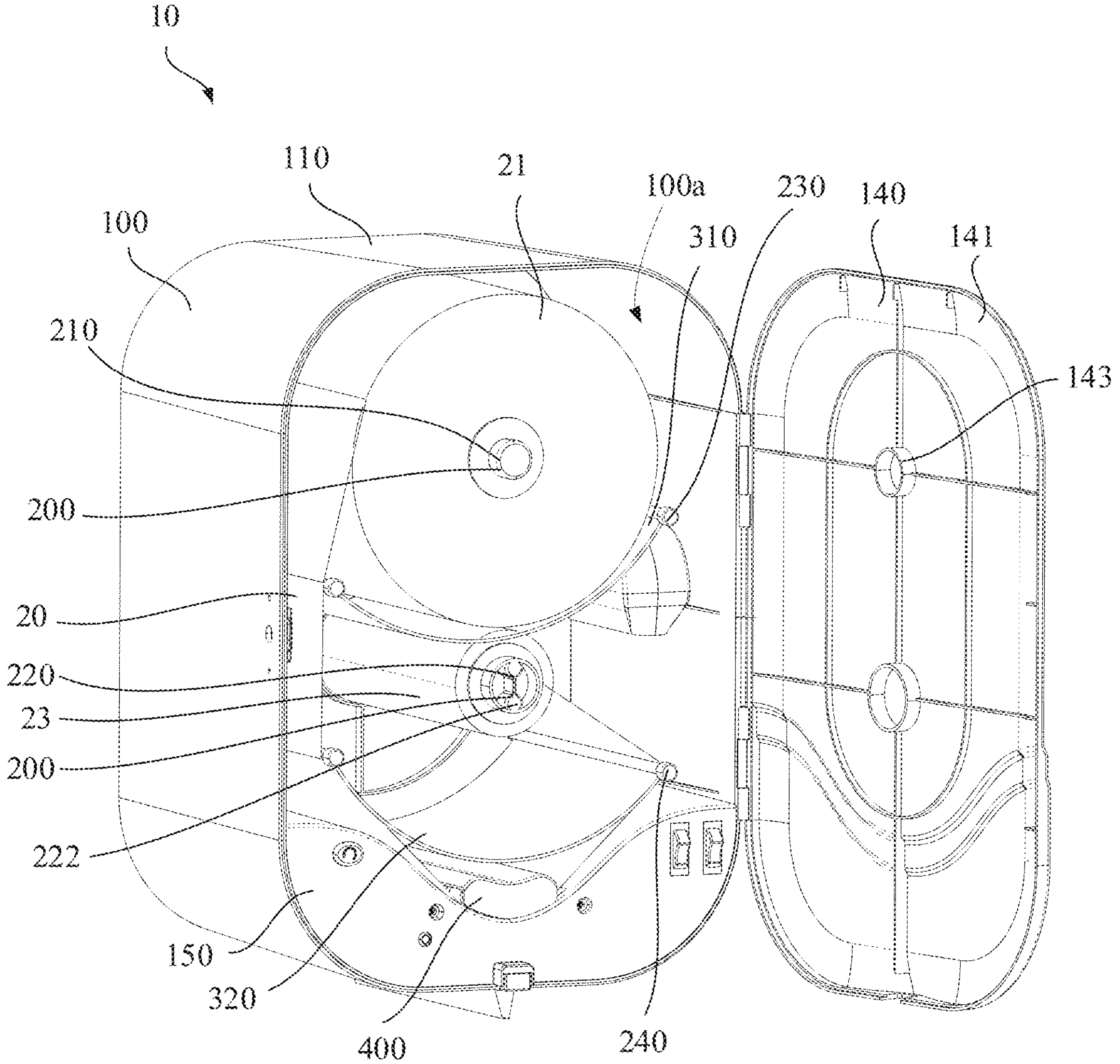
FIG. 8 is a schematic diagram of a fabric towel dispenser with a panel in an open state according to an embodiment of the present disclosure.

Referring to FIGS. 7 and 8, the fabric towel dispenser 10 includes a pressure roller 400 as well as a releasing drive roller 250 and a collecting auxiliary roller 260 that are arranged parallel and spaced within the shell 110. The pressure roller 400 includes a first roller 410, a second roller 420 arranged parallel to and spaced apart from the first roller 410, and a connecting piece 430 that connects the first roller 410 and the second roller 420. In addition, referring to FIG. 3, the releasing drive roller 250 is correspondingly arranged with the first roller 410 and is used to drive the unused new fabric towel 20 between the releasing drive roller 250 and the first roller 410 by means of the extrusion and traction effect, thereby moving the new fabric towel 20 out of the housing 100 through the fabric towel outlet 110*a*. The collecting auxiliary roller 260 is correspondingly arranged with the second roller 420 and is used to press the used fabric towel 20 between the collecting auxiliary roller 260 and the second roller 420 to make the used fabric towel 20 be more neatly rolled back into the housing 100.

In some embodiments, the pressure roller 400 may be connected to the structural components inside the middle plate 130 by an elastic element such as a spring or an elastic sheet in a floating manner. This ensures that the first roller 410 can apply an extrusion force to the unused new fabric towel 20, allowing it to be smoothly pulled toward the fabric towel outlet 110*a*, while also providing suitable floating space between the first roller 410 and the releasing drive roller 250 to reduce the motion resistance of the unused new fabric towel 20. Moreover, when replacing fabrics of different thicknesses, it can ensure that the fabric towel 20 smoothly moves out through the fabric towel outlet 110*a*, improving the versatility and adaptability of the fabric towel dispenser 10.

The pressure roller 400 and the structural components inside the middle plate 130 can be connected in a floating manner so as to ensure the extrusion force of the second roller 420 on the used fabric towel 20, so that the used fabric towel 20 can be smoothly and neatly collected into the housing 100. At the same time, a suitable floating space is provided between the second roller 420 and the collecting auxiliary roller 260 to reduce the motion resistance of the used fabric towel 20, ensuring that the fabric towel 20 is smoothly and neatly collected into the housing 100 even when the thickness of the fabric changes, enhancing the versatility and adaptability of the fabric towel dispenser 10.

Continuing with reference to FIG. 7, in some embodiments, the pressure roller 400 may be detachably or movably arranged in the housing 100. For example, the connecting piece 430 of the pressure roller 400 can be detachably connected to a baffle 150 by a snap connection method. During the process of installing the unused fabric roll 21, the pressure roller 400 can be removed from the baffle 150, and the entire pressure roller 400 can be moved out or swung and lifted, providing more space for hand operations and reducing the overall size of the fabric towel dispenser 10, improving the compactness of the structure.

It can be understood that in some embodiments, the second roller 420 and the connecting piece 430 are not necessary and can be omitted, or only one of them can be omitted. The collecting auxiliary roller 260 alone can guide the used fabric towel 20 toward the collecting shaft 220. Additionally, the first roller 410 and the second roller 420 can be independently arranged without being connected to each other, and both can be detachably or movably arranged in the housing 100.

Referring to FIG. 7, in the embodiment of the present application, the fabric towel dispenser 10 may include a collecting motor 510 and a releasing motor 520. The housing 100 may also include a baffle 150, which is connected to the shell 110 and forms an installation chamber 100*b* (refer to FIG. 5). The collecting motor 510 and the releasing motor 520 are both provided within the installation chamber 100*b*. The installation chamber 100*b* can be considered part of the cavity 100*a* separated by the baffle 150. An output end of the collecting motor 510 passes through the middle plate 130 and extends between the middle plate 130 and the back plate 120, and the collecting motor 510 is linked to the collecting shaft 220 via a belt drive structure. An output end of the releasing motor 520 also passes through the middle plate 130 and extends between the middle plate 130 and the back plate 120, and the releasing motor 520 is linked to the releasing drive roller 250 via another belt drive structure. During the operation of the fabric towel dispenser 10, the releasing motor 520 can start first for a preset time, and through the extrusion friction between the releasing drive roller 250 and the first roller 410, a preset length of the unused new fabric towel 20 is drawn out through the fabric towel outlet 110*a*. After the users have finished wiping their hands with the fabric towel 20, the collecting motor 510 then starts for a second preset time, and the used fabric towel 20 is drawn through the collecting auxiliary roller 260 and the second roller 420 via the collecting shaft 220, using the extrusion force between the collecting auxiliary roller 260 and the second roller 420 to neatly roll a preset length of the used fabric towel 20 onto the collecting shaft 220. The first preset time may be essentially the same as the second preset time.

In some embodiments, a distance of shafts between the releasing motor 520 and the releasing drive roller 250 is smaller than a distance of shafts between the collecting motor 510 and the collecting shaft 220. This arrangement allows for a shorter belt drive distance for the releasing motor 520, reducing the transmission loss of the releasing motor 520 while improving the compactness of the structure, thus saving energy.

Furthermore, the fabric towel dispenser 10 can achieve automated control by integrating an infrared sensor and controller. For example, by detecting the user's hand with an infrared sensor, the releasing motor 520 can be activated when the user's hand is placed in a certain area at the fabric towel outlet 110*a*, causing the unused new fabric towel 20 to be released outside the fabric towel outlet 110*a*. After the users removes their hand, the collecting motor 510 is activated to use the collecting shaft 220, in conjunction with the collecting auxiliary roller 260 and the extrusion effect between the second roller 420, to neatly roll the used fabric towel 20 onto the collecting shaft 220.

It is understood that as the fabric towel dispenser 10 continues to operate, the radial size of the used fabric towel roll 23 will increase. The same length of new fabric towel 20 is released out of the fabric towel outlet 110*a*, and after use, if the speed of the collecting motor 510 remains constant, the collecting time will become shorter. Therefore, further automation control can be implemented using a photoelectric sensor to keep the collecting time within a consistent range. For instance, multiple photoelectric sensors can detect the radial size of the used fabric towel roll 23 wound onto the collecting shaft 220. As the radial size of the roll increases, the speed of the collecting motor 510 is reduced in stages. For example, three photoelectric sensors can be set radially along the used fabric towel roll 23 on the housing 100, corresponding to three speed ranges for the collecting motor 510. Each time a sensor is blocked, the controller reduces the speed of the collecting motor 510 by one step, thereby maintaining a constant collecting time.

In other embodiments, the fabric towel dispenser 10 can include a UV sterilization component (not shown) within the cavity 100*a*. The UV sterilization component can be used to sterilize both the unused new fabric towel 20 and the used fabric towel 20, ensuring the cleanliness and hygiene of the new fabric towel 20 and maintaining hygiene inside the fabric towel dispenser 10.

The fabric towel dispenser 10 may also include an evaporation acceleration component (not shown) within the cavity 100*a*, which corresponds to the used fabric towel 20 and includes at least one of a blowing element and a heating element. When powered, the evaporation acceleration component can blow or heat the used fabric towel 20, increasing the evaporation rate of moisture from the fabric and keeping the interior of the fabric towel dispenser 10 dry, improving the user experience. Of course, a humidity sensor can be incorporated for automatic drying operation. The controller starts the evaporation acceleration component when the humidity exceeds a threshold, reducing the humidity inside the fabric towel dispenser 10 to maintain dryness and improve user experience.

The fabric towel dispenser 10 includes a housing 100 and a support shaft 200. The housing 100 includes a shell 110, a back plate 120, and a middle plate 130. The back plate 120 and middle plate 130 are fixedly connected to the shell 110, and the middle plate 130 and the shell 110 enclose a cavity 100*a* for containing fabric towel 20. The support shaft 200 passes through the middle plate 130, with one end connected to the back plate 120. The support shaft 200 is supported by both the middle plate 130 and back plate 120, with at least part of the shaft suspended on a side of the middle plate 130 facing away from the back plate 120 to support the fabric towel 20. The support shaft 200 has one end connected to the back plate 120, and the other end suspended in the cavity 100*a*. Through the joint support of the middle plate 130 and back plate 120, the back plate 120 and middle plate 130 can act as levers during the support of the fabric towel 20 by the shaft 200, and with appropriately rigid support shafts, there is no need for additional complex or high-strength support structures to maintain the rigidity of the support shaft 200. This simplifies the device structure, improves compactness, and saves space to ensure the volume of the cavity 100*a*. It also makes it easier for users to install the unused fabric roll 21 or remove the used fabric towel roll 23.

The technical features of the above embodiments can be combined in various ways. For simplicity, not all possible combinations of the technical features in the above embodiments are described. However, as long as these combinations do not conflict, they should be considered within the scope of this description.

The embodiments described above represent some of the implementations of the present disclosure, which are specific and detailed, but should not be understood as limiting the scope of the present disclosure's patent. It should be noted that modifications and improvements can be made by those skilled in the art without departing from the inventive concept, and these are within the scope of the present disclosure. Therefore, the protection scope of the present disclosure patent should be defined by the attached claims.

What is claimed is:

1. A fabric towel dispenser, comprising:

a housing, comprising a shell, a backplate, and a middle plate, wherein the backplate and the middle plate are fixed relative to the shell, and the middle plate and the shell enclose a cavity for storing a fabric towel;

a support shaft, having a first end and a second end opposite to the first end, wherein the support shaft passes through the middle plate, the first end is connected to the backplate, and a portion of the support shaft between the first end and the second end is supported by the middle plate, such that the support shaft is jointly supported by the middle plate and the backplate, and the second end of the support shaft is suspended, as a free end, on a side of the middle plate facing away from the backplate to support the fabric towel; and a panel connected to the shell and configured to switch between an open state and a closed state relative to the shell;

wherein, in the open state, the second end is exposed to allow a fabric roll to be mounted onto the support shaft or removed from the support shaft, and in the closed state, the panel covers the cavity.

2. The fabric towel dispenser according to claim 1, wherein the fabric towel dispenser comprises an ultraviolet (UV) sterilization module provided inside the cavity.

3. The fabric towel dispenser according to claim 1, wherein the fabric towel dispenser comprises an evaporation acceleration component provided inside the cavity; the evaporation acceleration component corresponds to the used fabric towel and comprises at least one of a blowing element and a heating element.

4. The fabric towel dispenser according to claim 1, wherein the support shaft comprises a collecting shaft for fixing a used fabric towel and is driven to rotate, winding the used fabric towel onto the collecting shaft.

5. The fabric towel dispenser according to claim 4, wherein the housing comprises a support slot configured to place a fabric roll to be used.

6. The fabric towel dispenser according to claim 4, wherein the support shaft further comprises a releasing shaft parallel to and spaced apart from the collecting shaft, and the releasing shaft passes through a fabric roll to be used.

7. The fabric towel dispenser according to claim 6, wherein a fabric towel outlet is provided below the shell for dispensing the fabric towel.

8. The fabric towel dispenser according to claim 6, wherein the fabric towel dispenser comprises a first flexible partition provided inside the cavity, the first flexible partition is provided between the releasing shaft and collecting shaft, the first flexible partition is able to adjust a curvature as a radial dimension of the fabric roll to be used or the used fabric towel roll changes.

9. The fabric towel dispenser according to claim 6, wherein in the open state, the releasing shaft and collecting shaft are exposed; the panel comprises a plate body and limit members that protrude from an inner side of the plate body; and in the closed state, the limit members limit a swinging range of free ends of the releasing shaft and the collecting shaft.

10. The fabric towel dispenser according to claim 4, wherein the fabric towel dispenser comprises a first roller provided inside the shell, as well as a releasing drive roller and a collecting auxiliary roller that are parallel and spaced apart; the releasing drive roller corresponds to the first roller and moves a new fabric towel through the fabric towel outlet to an exterior of the housing; and the collecting auxiliary roller is configured to guide the used fabric towel to the collecting shaft.

11. The fabric towel dispenser according to claim 10, wherein the fabric towel dispenser comprises a second roller, parallel to and spaced apart from the first roller, positioned opposite the collecting auxiliary roller and configured to cooperate with the collecting auxiliary roller to compress the used fabric towel between the collecting auxiliary roller and second roller.

12. The fabric towel dispenser according to claim 11, wherein the fabric towel dispenser comprises a connector, and the first and second rollers are connected to the connector.

13. The fabric towel dispenser according to claim 12, wherein the connector is detachably or movably installed in the housing.

* * * * *